United States Patent [19]
Wagner et al.

[11] Patent Number: 5,714,355
[45] Date of Patent: Feb. 3, 1998

[54] MICROORGANISM, USE THEREOF AND PROCESS FOR THE PRODUCTION OF L-α-AMINO ACIDS

[75] Inventors: Fritz Wagner; Britta Hantke; Thomas Wagner, all of Braunschweig; Karlheinz Drauz, Freigericht; Andreas Bommarius, Frankfurt, all of Germany

[73] Assignee: Degussa Aktiengesellschaft, Frankfurt, Germany

[21] Appl. No.: 654,670

[22] Filed: May 29, 1996

[30] Foreign Application Priority Data

May 30, 1995 [DE] Germany ............... 195 19 717.8

[51] Int. Cl.⁶ .................... C12P 13/04; C12P 13/06
[52] U.S. Cl. .................... 435/106; 435/107; 435/108; 435/109; 435/110; 435/113; 435/114; 435/115; 435/116; 435/830
[58] Field of Search ............... 435/830, 106–110, 435/113–116

[56] References Cited

U.S. PATENT DOCUMENTS

| | | | |
|---|---|---|---|
| 4,148,688 | 4/1979 | Yamada et al. | 195/29 |
| 5,108,914 | 4/1992 | Wagner et al. | 435/106 |
| 5,516,660 | 5/1996 | Wagner et al. | 435/106 |

*Primary Examiner*—Sandra A. Saucier
*Attorney, Agent, or Firm*—Cushman Darby & Cushman, IP Group of Pillsbury Madison & Sutro LLP

[57] ABSTRACT

DSM 9771 is a mutant of DSM 7330 which was obtained under selective pressure. Its enzymatic activity is higher by a factor of 2.3 than that of its parent organism. In the presence of an inducer, this activity may be farther increased by a factor of 2.7. The reaction catalyzed by this microorganism or enzymes therefrom is the enantioselective conversion of a D-5-monosubstituted hydantoin or an L-5-monosubstituted hydantoin or a D-N-carbamoyl amino acid or an L-N-carbamoyl amino acid to a corresponding L-α-amino acid.

5 Claims, 1 Drawing Sheet

MICROORGANISM, USE THEREOF AND PROCESS FOR THE PRODUCTION OF L-α-AMINO ACIDS

BACKGROUND OF THE INVENTION

1. Field of the Invention

This invention relates to a novel microorganism which is capable, at high specific activities, of converting D- or L- or D,L-5-monosubstituted hydantoins or D- or L-, or D,L-N-carbamoyl-α-amino acids into the corresponding, enantiomerically pure L-α-amino acids.

2. Background Information

Many methods have previously been described in the literature or been the subject matter of patent applications for the fermentational or enzymatic conversion of N-5-monosubstituted hydantoins into the enantiomerically pure L-α-amino acid (c.f. Syldatk, C., Müller, R., Pietzsch, M., Wagner, F., *Microbial and enzymatic production of L-amino acids from D,L-5-monosubstituted hydantoins* in Biocatalytic production of amino acids and derivatives (Rozell, J. D. and Wagner, F., eds.), Hanser Verlag, Munich, 1992, pp. 129–176).

Yokozeki, K., Sano, K., Eguchi, C., Iwagami, H. and Mitsugi, K. (1986): *Optimal conditions for the enzymatic production of L-aromatic amino acids from the corresponding 5-substituted hydantoins*, Agric. Biol. Chem. 51, 729–736 and Yokozeki, K., Hirose, Y. and Kubota, K. (1986): *Mechanism of asymmetric production of L-aromatic amino acids from the corresponding hydantoins by Flavobacterium sp.*, Agric. Biol. Chem., 51, 737–746 describe a reaction mechanism for the hydrolysis of 5-arylalkyl hydantoins exemplified by 5-benzylhydantoin with a purified hydantoinase from Flavobacter sp. AJ-3912. The relative rates of the forward and backward reactions were determined in these papers and it was shown that the forward reaction from D-5-benzylhydantoin to N-carbamoyl-D-phenylalanine proceeded distinctly more slowly than the hydrolysis of L-5-benzylhydantoin to N-carbamoyl-L-phenylalanine. No statement is made concerning the mechanism of enantioselective hydrolysis of 5-alkylhydantoins, as it was possible convert only trace quantities of D,L-5-methylthioethylhydantoin to N-carbamoyl-L-methionine.

Arthrobacter sp. DSM 7329 and DSM 7330 are known from DE 43 16 928 C2, which have elevated productivity and produce predominantly aliphatic L-amino acids, such as for example L-methionine, from D-, and/or L-, and/or D,L- form of a 5-monosubstituted hydantoin and/or from the corresponding N-carbamoyl amino acid and/or from a mixture of both mentioned classes of substances in accordance with the reaction scheme reproduced in FIG. 1. In this scheme, "alkyl" merely exemplifies the above-stated range of substrates. Arrow thickness denotes the observed reaction rates.

Although the specific activities of DSM 7329 and 7330 are not inconsiderable, in particular for the conversion of D,L-5-monosubstituted hydantoins via the N-carbamoyl-α-amino acids to L-α-amino acids, it has proved relatively disadvantageous in practice that technically adequate specific activities may only be achieved if an inducer is used. 5-Indol-3-ylmethyl-3-methylimidazolidine-2,4-dione (N3-IMH) is preferably used for this purpose. If this inducer is not used, the specific activity of the hydantoin-cleaving enzyme system in DSM 7329 and 7330 is clearly only relatively low.

SUMMARY OF THE INVENTION

In the light of the above-stated prior art, the object of the present invention is to provide further microorganisms which are simple to cultivate and produce enzymes which are capable of producing L-α-amino acids in relatively large quantities or at relatively high rates from D-, L- and/or D,L-5-monosubstituted hydantoin and/or a D-, L- and/or D,L-N-carbamoyl-α-amino acid. A corresponding process for the production of L-α-amino acids and the use of the microorganisms constitute further objects.

This object is achieved with the microorganism DSM 9771. This microorganism was deposited on 28.02.1995 at DSM, Deutsche Sammlung von Mikroorganismen und Zellkulturen GmbH, Mascheroder Weg 1B, D-38124 Braunschweig and the corresponding certificates accompany the specification.

DSM 9771 is a mutant of the strain Arthrobacter sp. DSM 7330 obtained by natural selection. DSM 9771 exhibits the following substantial advantages over the parent organism:

- constitutional production of the hydantoin-cleaving enzyme system at a higher specific activity than DSM 7330. In this manner, it is particularly advantageously possible in a production process to dispense with an inducer such as 5-indol-3-ylmethyl-3-methylimidazolidine-2,4-dione (N3-IMH) which is otherwise necessary.
- accelerated cell growth due to absence of inducer.
- if desired, the specific activity of the microorganism may be still further increased by induction with N3-IMH.
- the biotransformation of 5-methylthioethylhydantoin to L-methionine by resting DSM 9771 cells proceeds stereoselectively (99.8% enantiomerically pure).
- conversion of the substrate at very high concentration proceeds virtually quantitatively within 48 hours (yield>90%).

Strain DSM 9771 is particularly markedly distinguished from the parent organism DSM 7330 in that it exhibits higher enzymatic activity (by a factor of 2.3) without induction of the enzyme system with the inducer 5-indol-3-ylmethyl-3-methylimidazolidine-2,4-dione (N3 -IMH). This was surprising and not straightforwardly predictable for the person skilled in the art. In particular, it was not obvious that it was specifically this mutant which exhibited the outstanding characteristics. Moreover, dispensing with the use of the inducer particularly advantageously results in distinctly faster cell growth.

Finally, as already stated, DSM 9771 may also be used in the presence of a conventional inducer. In this manner, it is, for example, possible to increase enzyme activity by a factor of 2.7 by cultivating microorganism DSM 9771 in the presence of the inducer N3-IMH.

The process for the production of L-α-amino acids by enzymatic conversion of a D-, or L-, or D,L-5-monosubstituted hydantoin or D-, or L-, or D,L-N-carbamoyl-α-amino acid is performed by the conversion proceeding by means of microorganism DSM 9771 and/or by means of enzymes produced by this microorganism. By virtue of the novel microorganism and the greatly improved specific activities and yields during the process, the process of the invention is also not obvious by analogy with a process known, for example, from DE 43 16 928 C2.

The process itself may in principle be performed by:
(a) resting or killed cells
(b) a mash of the microorganism
(c) a crude extract
(d) enzymes from the microorganism purified to a greater or lesser extent.

If the process is performed with the microorganism itself, this is best achieved with resting or killed cells, so that the cells do not themselves utilise the substrate.

If the process proceeds by means of the enzymes produced by the microorganism, this may be achieved with a mash of the microorganisms (for example obtained with a French press or glass bead mill), a crude extract or enzymes from the microorganism purified to a greater or lesser extent.

The stated process for the production of L-α-amino acids with the microorganism of the present invention or the enzymes thereof proceeds stereospecifically (99.8% enantiomerically pure).

The present invention also relates to the use of the microorganism DSM 9771 for cultivating mutants or variants of this microorganism or for obtaining a gene coding a carbamoylase and/or hydantoinase and/or hydantoinracemase or for inserting a gene coding a carbamoylase and/or hydantoinase and/or hydantoinracemase into a microorganism or cell or for producing an L-α-amino acid.

Cultivation of mutants or variants of the microorganism DSM 9771 may proceed, for example, by the selection of spontaneously occurring mutations. Other options are, for example, mutations arising from the action of chemical agents and/or radioactive radiation and/or UV light.

The purpose of obtaining one or more genes from the microorganism is, for example, to sequence the genes for the enzymes or to insert them into a microorganism, wherein by selecting the microorganism into which the gene is inserted, a microorganism may be obtained which produces larger quantities of the enzyme or enzymes vital to the above-stated process. The gene may optionally also be introduced into an animal or plant cell. Introduction of the gene proceeds using conventional microbiological methods, for example by means of a vector.

The stated novel microorganism produces large quantities of a series of enzymes, as a consequence of which the activity of the cell mass is extremely high for the above-stated process. No strains have hitherto been discovered which have a higher activity for this process.

The general range of substrates for microorganism DSM 9771 corresponds to the range of substrates stated in DE 43 16 928 C2 for the microorganisms DSM 7329 and DSM 7330.

DETAILED DESCRIPTION OF THE INVENTION

Figure 1:
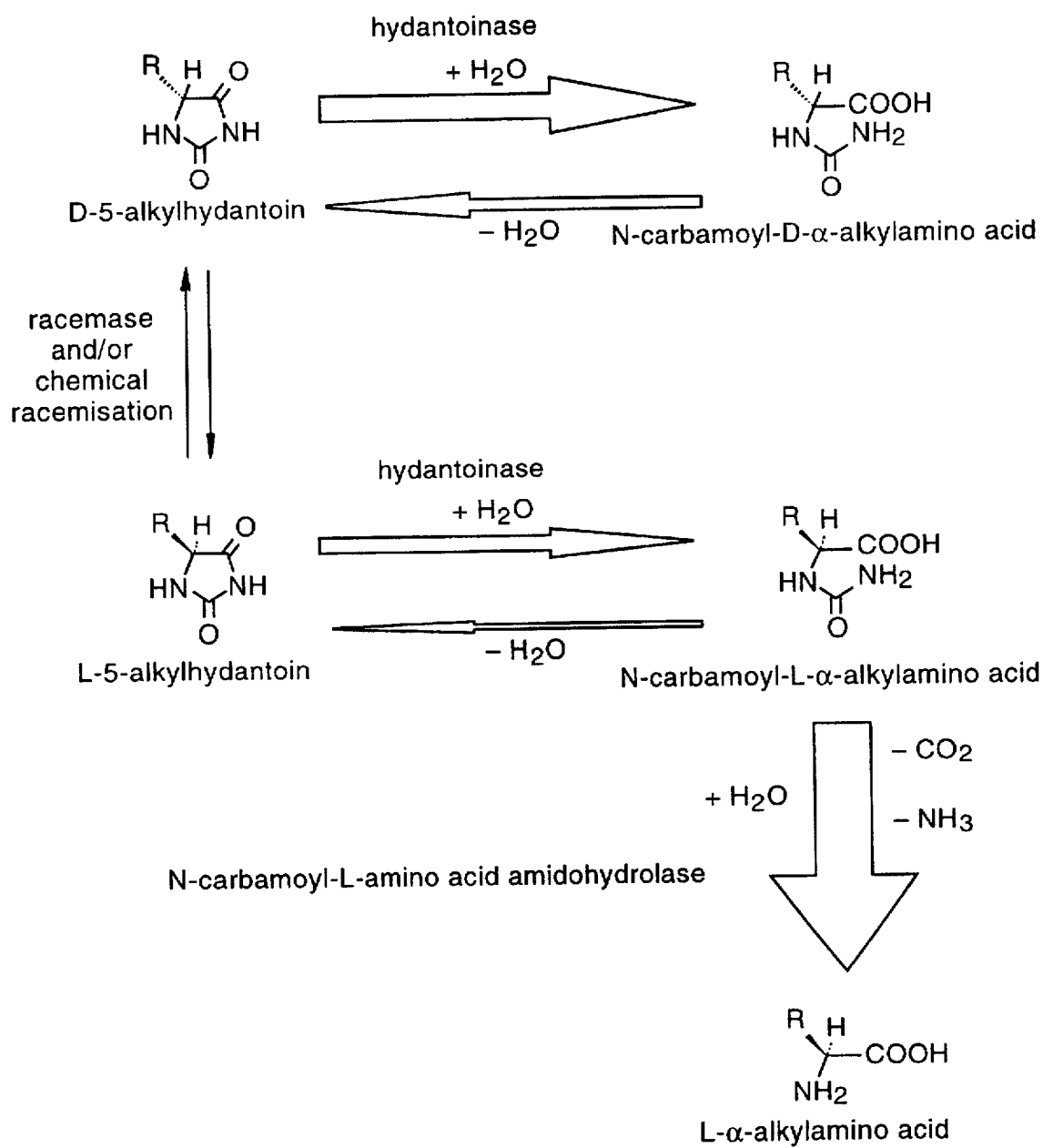
FIG. 1: Reaction scheme for the production of L-α-alkylamino acids

According to the reaction scheme stated above, the most varied 5-substituted hydantoins are converted into L-α-amino acids. According to the invention, the residue in the hydantoin may be an alkyl residue, be branched, be cyclic, be substituted with one or more heteroatoms, be aromatic, be heteroaromatic etc.. Difficulties occur only with 5-methylhydantoin, 5,5-disubstituted hydantoins, polysubstituted phenylhydantoins, such as 5-3'-methyl-4'-aminomethylphenylhydantoin, bulky substituents directly on the hydantoin, such as 5-t-butylhydantoin, together with residues having charged substituents close to the hydantoin, such as for example, 5-β-carboxylethylhydantoin, 5-γ-aminopropylhydantoin, 5-δ-aminobutylhydantoin. In contrast, a wide variety of compounds may be converted, such as, for example, 5-substituted hydantoins with the substituents isopropyl, n-propyl, n-butyl, methylthioethyl, isobutyl, indolylmethyl, cyclohexylmethyl, benzyl, naphthylmethyl, phenyl, wherein the most varied substituents are possible, for example on the benzyl, p-fluorine, p-chlorine, p-amino, p-methoxy, p-carboxyl. It is thus not possible to state any particular fundamental with regard to the 5-substituents on the hydantoin or the carbamoylamino acid, since by virtue of the wide variety of possible substituents and the wide variety of possible functionalisations of the substituents or of the amino acid residues, it is in principle possible to consider any typical 5-substituted hydantoins or the corresponding N-carbamoylamino acids as a substrate.

With regard to the differentiation of DSM 9771 from DSM 7329 and from the parent organism 7330, there is, in addition to the outstanding specific activity of the microorganism according to the invention, a further differentiating criterion that DSM 9771 is capable of utilising glycerol as well as citric acid. Neither DSM 7329 nor DSM 7330 were capable of this.

Reference is hereby made to DE 43 16 928.7 for delimitation from other known microorganisms, to which patent reference is expressly made for the purposes of disclosure. On the basis of the disclosure in DE 43 16 928.7, it is clear that neither DK-200 (EP-A-0 159 866), nor DSM 3745, DSM 3746, DSM 3747 (DE 37 12 539 C2), nor DSM 3306 (DE 37 02 384 A1, corresponds to U.S. Pat. No. 5,071,752), nor DP-B-1001, DP-B-1002 (Japanese patent (B2) Hei 4-39316) are capable of calling the novelty of the present microorganism into question. The formation of L-methionine from D,L-5-methylthioethylhydantoin with *Arthobacter ureafaciens* described by Guivarch et al. in *Bull. Soc. Chim. Fr*, no. 1–2, 91–95 describes a reaction path which does not occur in microorganism DSM 9771, and Japanese document Sho 55-29678 and Japanese publication JP-B-29678/80 likewise describe processes which clearly differ from the process as performed with microorganism DSM 9771 according to the invention.

As already mentioned, with regard to its physiological and bacteriological characterisation, DSM 9771 is substantially identical to microorganism DSM 7330. At variance with patent DE 43 16 928.7, microorganism 9771 is, however, capable of utilising glycerol as a source of carbon as well as citric acid.

The specific activities of complete cells were calculated using the following equation:

$$A_{spec} = \frac{\text{mmol or g of converted substrate}}{\text{g biomass wet weight} * h}$$

DSM 7330 has the following specific activity for D,L-methylthioethylhydantoin:

$$A_{spec} = \frac{28.7 \text{ (mmol)}}{50 (\text{g biomass wet weight}) * 7(h)} =$$

$$0.082 \left( \frac{\text{mmol}}{\text{g biomass wet weight} * h} \right)$$

Under identical conditions, strain DSM 9771 has the following specific activity for D,L-methylthioethylhydantoin:

$$A_{spec} = \frac{28.7 \text{ (mmol)}}{50 (\text{g biomass wet weight}) * 3(h)} =$$

$$0.191 \left( \frac{\text{mmol}}{\text{g biomass wet weight} * h} \right)$$

i.e. an increase of the specific activity for D,L-MTEH by a factor of 2.3. Using a higher substrate concentration and twice the wet cell weight, the following specific activity was determined:

$$A_{spec} = \frac{86.1 \text{ (mmol)}}{100(\text{g biomass wet weight}) * 2(h)} =$$

$$0.43 \left( \frac{\text{mmol}}{\text{g biomass wet weight} * h} \right)$$

i.e. a further increase by a factor of 2.3. The following specific activity was determined when using wet cell mass induced by means of N3-IMH during cultivation:

$$A_{spec} = \frac{86.1 \text{ (mmol)}}{100(\text{g biomass wet weight}) * 0.75(h)} =$$

$$1.148 \left( \frac{\text{mmol}}{\text{g biomass wet weight} * h} \right)$$

i.e. a further increase by a factor of 2.7 or, relative to DSM 7330, by a factor of 14.

EXAMPLE 1

Obtaining the mutant

The mutant DSM 9771 could be obtained by cultivating wild strain DSM 7330 under selective pressure. Selective pressure was exerted by L-carbamoylmethionine (L-CAM) as the sole source of nitrogen. Cultivation was performed in 500 ml shaken flasks containing 100 ml of selection medium for 3 days at 30° C. over 10 cycles. The inoculum used for the starter culture was 10 mg of biomass wet weight of DSM 7330. 5 ml of the previous culture was in each case used for the following cultivation.

Selection medium:

| | | |
|---|---|---|
| Glucose | 10.0 g/l | |
| KH$_2$PO$_4$ | 0.95 g/l | |
| K$_2$HPO$_4$*3H$_2$O | 2.0 g/l | |
| MgSO$_4$*7H$_2$O | 0.2 g/l | |
| CaCl$_2$*2H$_2$O | 0.02 g/l | |
| Trace salt solution | 10.0 ml/l | |
| pH 7.0 | | |
| L-CAM | 2.0 g/l | (added as sterile-filtered solution) |

Trace salt solution:

| | |
|---|---|
| Citric acid*H$_2$O | 150 mg/l |
| H$_3$BO$_4$ | 50 mg/l |
| CUSO$_4$*5H$_2$O | 4 mg/l |
| FeCl$_3$*6H$_2$O | 20 mg/l |
| MnSO$_4$*7H$_2$O | 40 mg/l |
| ZnSO$_4$*7H$_2$O | 40 mg/l |
| KI | 10 mg/l |
| Ammonium heptamolybdate | 20 mg/l |

In order to isolate individual colonies, a dilution was plated onto agar plates with selection medium after the 10th cultivation and the plates incubated for 4 days at 30° C. The isolated colonies were selected, cultivated in sloped agar tubes with complex medium 1 and stored at 4° C. In order to obtain biomass for the subsequent activity tests, the clones were cultivated for 14–16 hours at 30° C. in complex medium 2.

Complex medium 1 is of the following composition:

| | |
|---|---|
| Industrial yeast extract | 10.0 g/l |
| Bacto-peptone | 10.0 g/l |
| Glucose | 10.0 g/l |
| NaCl | 3.0 g/l |
| MgCl$_2$*4H$_2$O | 0.1 g/l |
| Trace salt solution | 10.0 ml/l |
| Agar | 15.0 g/l |
| pH | 7.0 |

Complex medium 2 is of the following composition:

| | | |
|---|---|---|
| Industrial yeast extract | 1.0 g/l | |
| Glucose | 10 g/l | added by pipette as sterile solution |
| K$_2$HPO$_4$*3H$_2$O | 7.61 g/l | added by pipette as sterile solution |
| KH$_2$PO$_4$ | 4.54 g/l | added by pipette as sterile solution |
| (NH$_4$)$_2$SO$_4$ | 6.5 g/l | |
| Citric acid*H$_2$O | 0.32 g/l | |
| MgSO$_4$*7H$_2$O | 0.20 g/l | |
| CaCl$_2$*2H$_2$O | 0.02 g/l | |
| MnCl$_2$*4H$_2$O | 0.02 g/l | |
| FeSO$_4$*7H$_2$O | 0.02 g/l | |
| pH | 6.8 | |

The enzymatic activity of the resultant wet cell mass (biomass wet weight) is comparatively tested under the following conditions: 800 μl of 0.1M tris-HCl buffer pH 8.5 are combined with 1 mg of D,L-5-methylthioethylhydantoin (D,L-MTEH) and 200 μl of a 10% cell suspension and cultivated for 3 h at 37° C. The cell suspension is then centrifuged and the clear supernatant analysed by HPLC.

The clone deposited with the Deutsche Sammlung für Mikroorganismen (DSM) proved to be particularly active. Classification of the strain revealed that it was a new species of the Arthrobacter group.

Table 1 shows examples of the conversions of D,L-5-monosubstituted hydantoins which may be hydrolysed with the microorganism according to the invention via the N-carbamoyl-α-amino acids to L-α-amino acids in accordance with the indicated reaction mechanism.

TABLE 1

| R = | Quantity introduced [mmol] | D,L-hydantoin [mmol] | N-carbamoyl derivative [mmol] | L-α-amino acid [mmol] |
|---|---|---|---|---|
|  | 28.7 | 6.60 | 11.01 | 10.74 |
| | | 11.09 | 11.7 | 5.48 | methylthioethyl

TABLE 1-continued

| R = | Quantity introduced [mmol] | D,L-hydantoin [mmol] | N-carbamoyl derivative [mmol] | L-α-amino acid [mmol] |
| --- | --- | --- | --- | --- |
|  iso-butyl | 32 | n.d.<br>n.d. | n.d.<br>n.d. | +<br>+ |
| 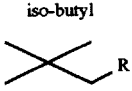 tert.-butyl | 32 | n.d.<br>n.d. | n.d.<br>n.d. | −<br>− |
|  benzyl | 26.3 | −<br>− | 2.0<br>4.82 | 27.19<br>22.94 |
| 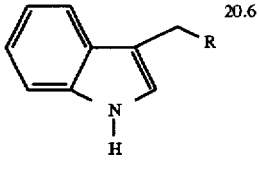 indolylmethyl | 20.6 | −<br>− | 0.34<br>2.41 | 20.32<br>18.15 |
| 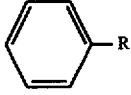 phenyl | 28.38 | 8.5<br>22.43 | n.d.<br>n.d. | n.d.<br>n.d. |

Reaction conditions: The stated concentration of substrate is incubated in 10 ml of 1M tris-HCL buffer pH 8.5 with 0.5 g of biomass wet weight for 4 hours at 37° C.

Bold print denotes induced cells; n.d.=not determinable; +=detectable; −=not detectable.

EXAMPLE 2

Cultivation of biomass

Four 500 ml conical flasks containing 100 ml of complex medium 1 (see above) were inoculated with 10 mg of biomass wet weight of strain DSM 9771 from a fresh sloped agar culture and cultivated for 23 hours at 30° C. and 100 rpm. Ten 2000 ml conical flasks each containing 500 ml of complex medium 3 are each inoculated with 25 ml of the first preliminary culture and incubated for 14 hours at 30° C. and 100 rpm. On completion of the incubation period, this preliminary culture II acts as the inoculum for a 50 l bioreactor. This reactor is equipped with an Intensive stirrer. 45 l of complex medium 4 are introduced and sterilised for 30 minutes at pH 6.8 and a temperature of 121° C. at a pressure of approximately 1 bar above atmospheric. The nutrient medium is optionally combined with 0.5 g/l of N3-IMH. After cooling to 30° C., the pH is adjusted to 7.0 with 10% NaOH and the mixture then inoculated with the suspended culture from preliminary culture II. Cultivation is performed at 30° C. and a stirrer speed of 400 rpm and an aeration rate of 0.8 V/V/m. After 11.5 h or 15 h in the case of induced cultivation, the cell suspension is centrifuged off. The resultant wet cell mass may be used for the enzymatic conversion either immediately or after interim storage at −18° C. 2.8 kg or 2.6 kg (induction) of wet cell mass are obtained.

| Complex medium 3: | | |
| --- | --- | --- |
| Industrial yeast extract | 0.75 g/l | |
| Glucose | 10 g/l | added by pipette as sterile solution |
| $K_2HPO_4*3H_2O$ | 7.61 g/l | added by pipette as sterile solution |
| $KH_2PO_4$ | 4.54 g/l | added by pipette as sterile solution |
| $(NH_4)_2SO_4$ | 4.0 g/l | |
| Citric acid*$H_2O$ | 0.32 g/l | |
| $MgSO_4*7H_2O$ | 0.20 g/l | |
| $CaCl_2*2H_2O$ | 0.02 g/l | |
| $MnCl_2*4H_2O$ | 0.02 g/l | |
| $FeSO_4*7H_2O$ | 0.02 g/l | |
| pH | 6.8 | |
| Complex medium 4: | | |
| Industrial yeast extract | 0.75 g/l | |
| Glucose | 20 g/l | added by pipette as sterile solution |
| $K_2HPO_4*3H_2O$ | 0.761 g/l | added by pipette as sterile solution |
| $KH_2PO_4$ | 0.454 g/l | added by pipette as sterile solution |
| $(NH_4)_2SO_4$ | 4.0 g/l | |
| Citric acid*$H_2O$ | 0.64 g/l | |
| $MgSO_4*7H_2O$ | 0.40 g/l | |

| | |
|---|---|
| $CaCl_2 \cdot 2H_2O$ | 0.04 g/l |
| $MnCl_2 \cdot 4H_2O$ | 0.04 g/l |
| $FeSO_4 \cdot 7H_2O$ | 0.04 g/l |
| pH | 6.8 |

EXAMPLE 3

15 g of uninduced wet cell mass of DSM 9771 and 2.25 g of D,L-MTEH (13 mmol) are resuspended in 150 ml of saline and incubated for 30 hours in a 250 ml stirred reactor at 37° C., pH 8.5, under an $N_2$ atmosphere and with constant-pH reaction control. The cells are then centrifuged off and the supernatant analysed by high pressure liquid chromatography (HPLC). 1.6 g (10.74 mmol) of L-methionine are detected in the supernatant.

Yield=82.6% of theoretical.

EXAMPLE 4

15 g of induced wet cell mass of DSM 9771 and 2.25 g of D,L-MTEH (13 mmol) are resuspended in 150 ml of saline and incubated for 30 hours in a 250 ml stirred reactor at 37° C., pH 8.5, under an $N_2$ atmosphere and with constant-pH reaction control. The cells are then centrifuged off and the supernatant analysed by high pressure liquid chromatography (HPLC). 1.7 g (11.4 mmol) of n-methionine are detected in the supernatant.

Yield=87.8% of theoretical.

EXAMPLE 5

Determination of Optimal pH

In order to determine DSM 9771's optimal pH for the biotransformation of D,L-MTEH to L-methionine, conversions were performed with a glycylglycine/piperazine buffer over a pH range from 5.0 to 10.5. The assay was performed in 100 ml shaken flasks with two flow spoilers. 9 ml of 0.1M glycylglycine/piperazine buffer, in which 1 g/l of D,L-MTEH had already been dissolved, were introduced into the flasks. The biocatalyst used was 1 ml of a 50% biomass wet weight/saline suspension of DSM 9771 and incubation was performed for 3.5 hours in a shaken water bath under an $N_2$ atmosphere at 37° C.

In the pH range between 8.0 and 9.0, the substrate had been completely broken down after only 1 hour. In contrast, the highest Met concentration was measured at pH 8.0. After 2 hours' incubation, this optimum shifts to the pH range from 7.0 to 8.0, at which the substrate is also completely broken down. The following conversions were performed at a pH value of 7.5, as formation of the L-amino acid is promoted at this pH.

EXAMPLE 6

Determination of Optimal Temperature

Testing to determine the optimal temperature for the hydrolysis of D,L-MTEH to L-Met with DSM 9771 as the biocatalyst was also performed in 100 ml shaken flasks. The substrate solution used was 5 g/l of D,L-MTEH in 0.1M tris-HCl buffer pH 7.5. Two flasks containing buffer/substrate solution were preincubated for each temperature (25° C.; 30° C., 34° C., 37° C., 40° C., 45° C. and 50° C.) and the reaction was then started with 1 ml of a 50% biomass wet weight/saline suspension. Reaction kinetics were recorded over 5 hours for each temperature. An optimal temperature of 34°–37° C. was determined for the above-stated reaction after 2 hours' incubation, which corresponds to the optimal temperature for the wild strain DSM 7330.

EXAMPLE 7

140 g of induced wet cell weight of DSM 9771 and 42 g of D,L-MTEH (24 mmol) are resuspended in 1400 ml of saline and incubated for 8.5 hours in a 1500 ml stirred reactor at 37° C., under an $N_2$ atmosphere and with constant-pH reaction control. After centrifugation, 32.8 g (220 mmol) of L-methionine are detected in the supernatant.

Yield=91% of theoretical.

EXAMPLE 8

140 g of induced wet cell weight of DSM 9771 and 42 g of D,L-MTEH (241 mmol) are resuspended in 1400 ml of saline and incubated in a 1500 ml stirred reactor at 34° C., under an $N_2$ atmosphere and with constant-pH reaction control. At 1.5 hour intervals, nine 14 g (80.4 mmol) portions of D,L-MTEH are apportioned. After 48 hours, the reaction is terminated. Since the product L-methionine is present in crystalline form, the reaction solution is diluted with three times its volume of saline. The cells are then centrifuged off and the supernatant analysed by high pressure liquid chromatography (HPLC). 142 g (952 mmol) of L-methionine are detected in the supernatant.

Yield=98.8% of theoretical.

What is claimed is:

1. A biologically pure culture assigned accession number DSM 9771.

2. A process for the production of an L-α-amino acid comprising the step of incubating the microorganism of claim 1 and/or enzymes therefrom which are capable of converting compounds selected from the group consisting of a D-5-monosubstituted hydantoin, an L-5-monosubstituted hydantoin, a D-N-carbamoyl amino acid and an L-N-carbamoyl amino acid to an L-α-alkyl amino acid, in a solution containing at least one compound selected from said group, so that said compound is enzymatically converted to said L-α-amino acid, and detecting said L-α-amino acid.

3. The process of claim 2 wherein said microorganism is a resting microorganism.

4. The process of claim 2 wherein said solution contains a racemic mixture of a D,L-5-monosubstituted hydantoin.

5. The process of claim 2 wherein said solution contains a racemic mixture of a D,L-N-carbamoyl amino acid.

* * * * *